United States Patent [19]
Hamano et al.

[11] Patent Number: 5,879,692
[45] Date of Patent: Mar. 9, 1999

[54] TOCOPHERYL ASCORBYL PHOSPHATE-CYCLODEXTRIN CLATHRATE AND A TOPICAL DERMAL COMPOSITION CONTAINING SAID CLATHRATE

[75] Inventors: Yohei Hamano; Hajime Matsuda, both of Yokohama; Hideyuki Sumiyoshi, Fuji, all of Japan

[73] Assignee: Senju Pharmaceutical Co., Ltd.

[21] Appl. No.: 917,137

[22] Filed: Aug. 25, 1997

[51] Int. Cl.$^6$ ....................................................... A61K 7/00
[52] U.S. Cl. ........................................... 424/401; 514/887
[58] Field of Search ....................... 424/401, 63; 514/887

[56] References Cited

U.S. PATENT DOCUMENTS 4,831,022  5/1989  Hijiya .......................................... 514/58

*Primary Examiner*—Gollamudi S. Kishore
*Assistant Examiner*—D. Faulkner
*Attorney, Agent, or Firm*—Wenderoth, Lind & Ponack, L.L.P.

[57]  ABSTRACT

The invention provides a clathrate comprising a cyclodextrin or hydroxyalkylated cyclodextrin and, as included therein, dl-α-tocopheryl L-ascorbyl phosphate. In another aspect, the invention provides a dermal composition for external use, particularly a cosmetic composition. The composition is characterized by reduced foam production in aqueous solution and good stability against light.

9 Claims, 10 Drawing Sheets

EPC-K

HP-β-CD

HP-β-CD : EPC-K = 1 : 1 COMPLEX

HP-β-CD : EPC-K = 2 : 1 COMPLEX

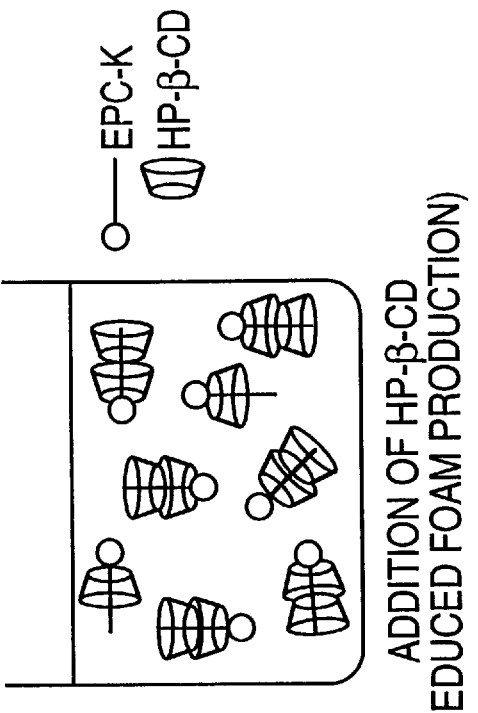
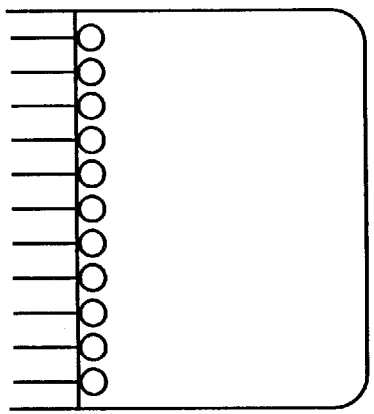
FIG. 1a
OMISSION OF HP-β-CD
(COPIOUS FOAM PRODUCTION)
FIG. 1b
ADDITION OF HP-β-CD
(REDUCED FOAM PRODUCTION)
○— EPC-K
⊕ HP-β-CD

EPC-K

HP-β-CD

HP-β-CD : EPC-K = 1 : 1 COMPLEX

HP-β-CD : EPC-K = 2 : 1 COMPLEX

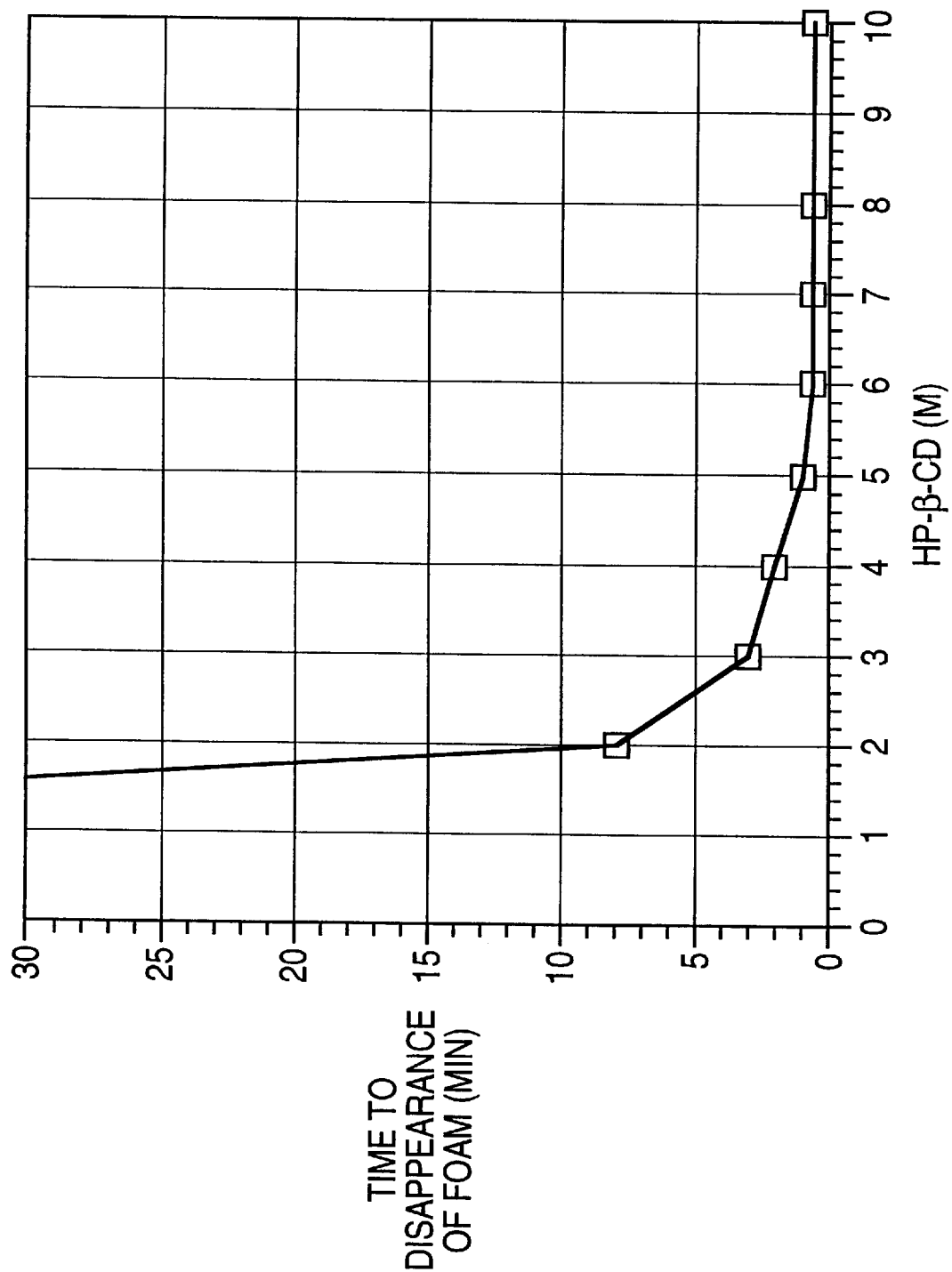

EPC-K 10 mM/D₂O

EPC-K + HP-β-CD 10 mM/D₂O
(EPC-K : HP-β-CD = 1:1)

HP-β-CD 10 mM/D₂O
(REF. ACETONE)

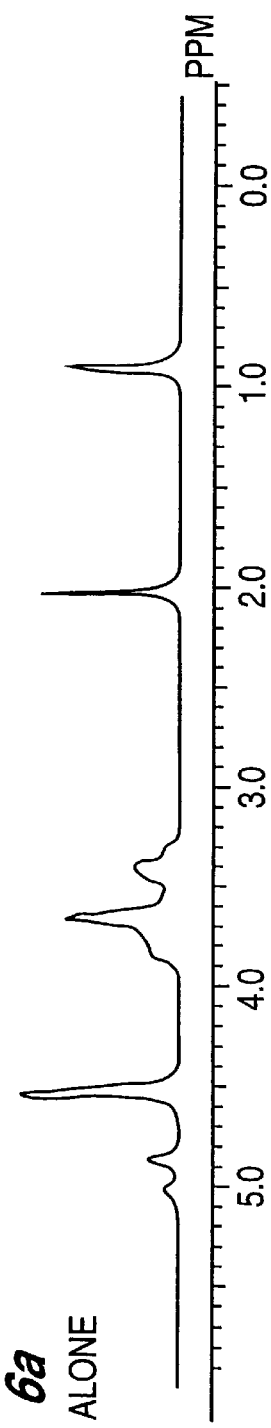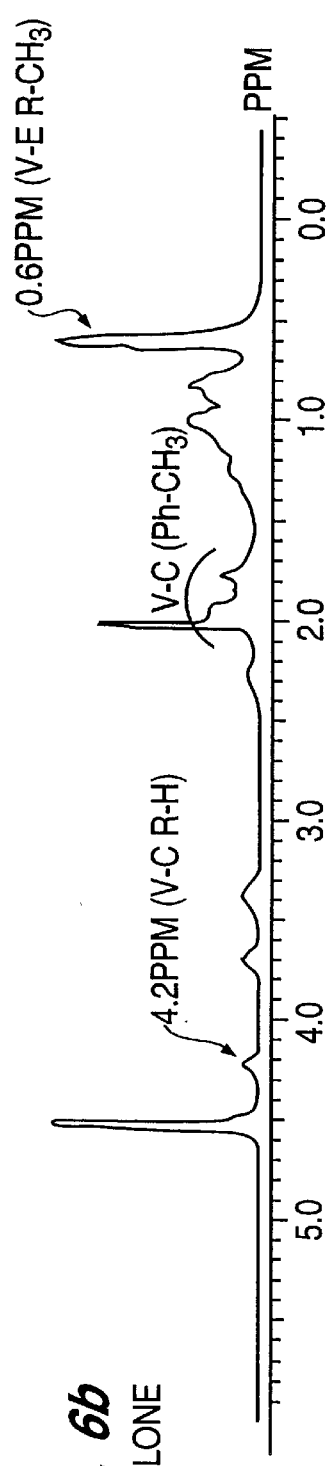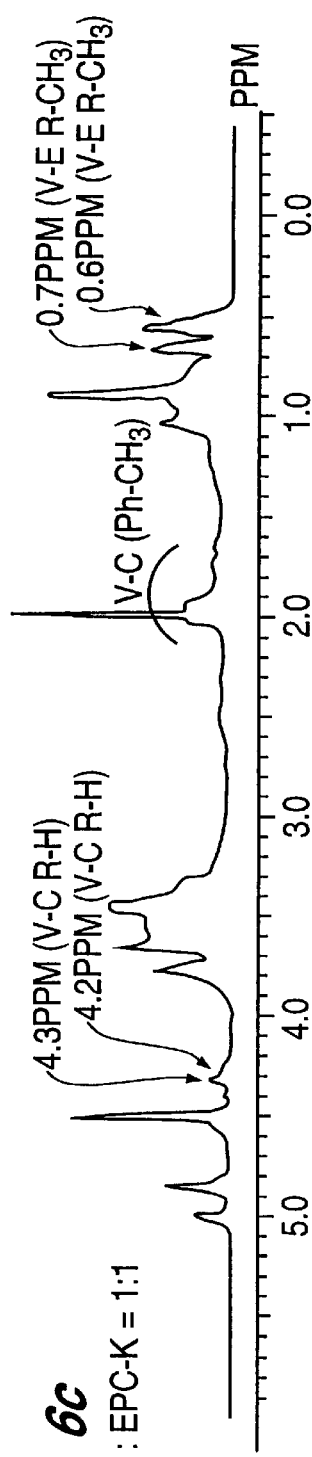
FIG. 6a  1) HP-β-CD ALONE
FIG. 6b  2) EPC-K ALONE
FIG. 6c  3) HP-β-CD : EPC-K = 1:1

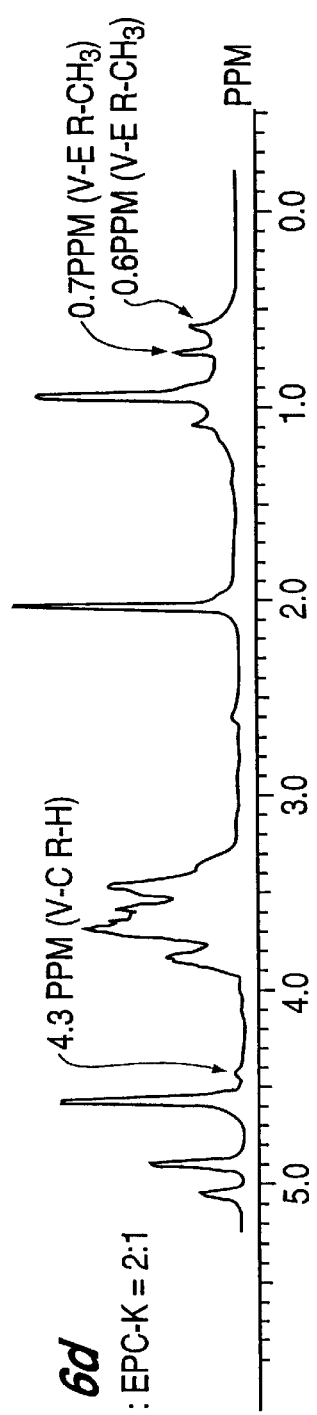
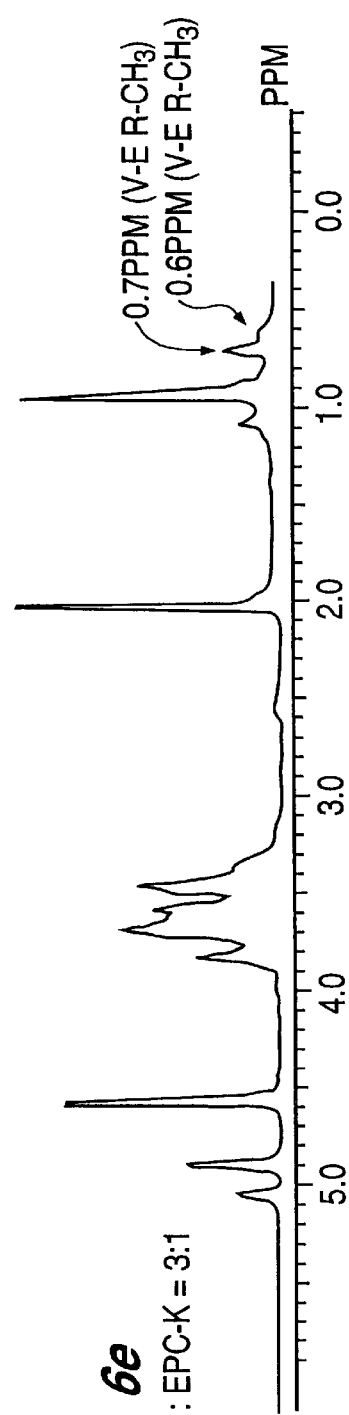
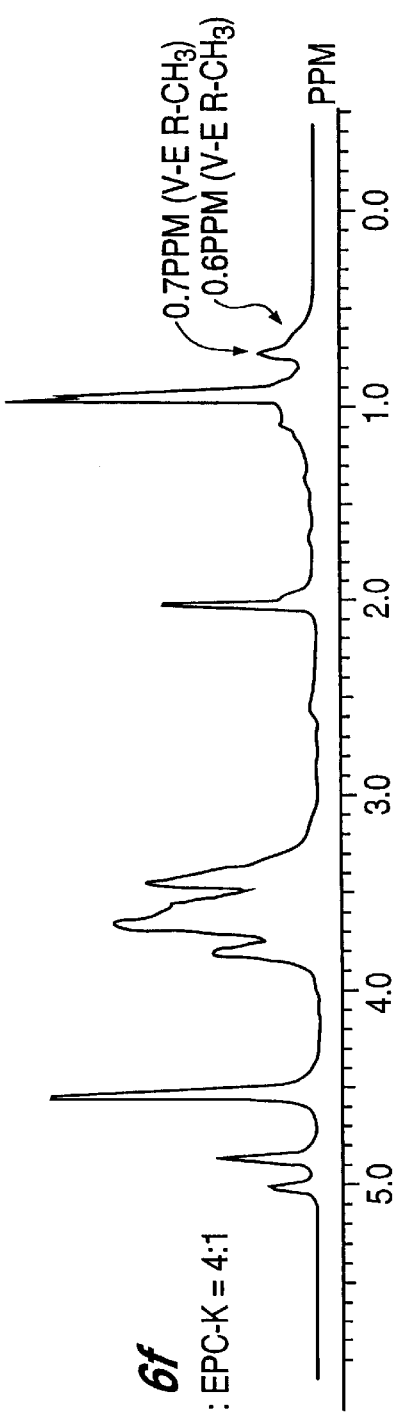
FIG. 6d
4) HP-β-CD : EPC-K = 2:1
FIG. 6e
5) HP-β-CD : EPC-K = 3:1
FIG. 6f
6) HP-β-CD : EPC-K = 4:1

1) EPC-K ALONE

2) HP-β-CD : EPC-K = 1:1

3) HP-β-CD : EPC-K = 2:1

4) HP-β-CD : EPC-K = 3:1

5) HP-β-CD : EPC-K = 5:1

1) EPC-K ALONE

2) HP-β-CD : EPC-K = 0.5 : 1

3) HP-β-CD : EPC-K = 1 : 1

5) HP-β-CD : EPC-K = 2 : 1

TOCOPHERYL ASCORBYL PHOSPHATE-CYCLODEXTRIN CLATHRATE AND A TOPICAL DERMAL COMPOSITION CONTAINING SAID CLATHRATE

FIELD OF THE INVENTION

The present invention relates to a dl-α-tocopheryl L-ascorbyl phosphate-cyclodextrin clathrate and a topical dermal composition containing the clathrate, which is easy to use and has been improved in the stability of dl-α-tocopheryl L-ascorbyl phosphate.

BRIEF DESCRIPTION OF THE PRIOR ART

Retention of skin moisture is essential to the maintenance of the skin in healthy condition and a large number of cosmetic and pharmaceutical preparations designed for improved moisture retention, better skin condition, and enhanced resistance to oxidation have been launched on the market. While a variety of humectants and other chemicals are commercially available, dl-α-tocopheryl L-ascorbyl phosphate (vitamin E-vitamin C diester of phosphoric acid) (hereinafter referred to briefly as EPC) is a compound possessing not only humectant properties but also collagen production-activating and antioxidant activities and, as such, is broadly formulated, generally in the form of its potassium salt (hereinafter referred to briefly as EPC-K), in cosmetic products.

EPC-K is a water-soluble substance but because the alkyl side chain of its tocopheryl moiety is oleophilic and the ascorbic acid moiety is hydrophilic, it exhibits surface activity. Therefore, an aqueous solution of EPC-K produces a copious foam and, once it foams, the foam does not subside for a few days, thus causing considerable difficulties in handling. Moreover, EPC-K is not sufficiently resistant to light so that when it is incorporated in a clear cosmetic solution, e.g. a lotion, the lotion discolors easily with time as can be recognized by a light exposure test using a xenone (Xe) lamp or sunlight.

OBJECT AND SUMMARY OF THE INVENTION

Developed to overcome the above disadvantages of the prior art, the present invention has for its object to provide a stable clathrate compound consisting of said EPC having humectant, collagen production-activating, and antioxidant properties and a host substance and, thus, contributory to reduced foam production and improved light stability and to provide a topical composition containing said clathrate for application to the skin.

After the intensive research done to accomplish the above object, the inventors of the present invention discovered that when the oleophilic alkyl side chain of the tocopheryl moiety of EPC is clathrated with a cyclodextrin or hydroxyalkylated cyclodextrin molecule, the surface activity of EPC is decreased with the result that not only the foam production of EPC in solution is reduced but its light stability is improved.

The clathrate of the present invention is characterized in that EPC is included in a cyclodextrin or hydroxyalkylated cyclodextrin.

In the above clathrate of the invention, the cyclodextrin or hydroxyalkylated cyclodextrin is preferably β-cyclodextrin or a hydroxyalkylated β-cyclodextrin.

Furthermore, in this clathrate of the invention, the molar ratio of (cyclodextrin or hydroxyalkylated cyclodextrin):EPC is preferably 1:1–2:1.

The topical dermal composition of the present invention is characterized in that it contains the above-mentioned clathrate.

The topical dermal composition of the present invention is preferably an oil-in-water emulsion.

Furthermore, the topical dermal composition of the invention is preferably an aqueous solution (e.g. a cosmetic lotion) prepared without addition of a surfactant.

In addition, the topical dermal composition contains said clathrate preferably in a proportion of 0.001–10 weight % based on the total weight of the composition.

The topical dermal composition of the present invention is further characterized in that it contains a cyclodextrin or hydroxyalkylated cyclodextrin and EPC.

Preferably, the topical dermal composition of the invention comprises 0.005–20 weight % of β-cyclodextrin or a hydroxyalkylated β-cyclodextrin, 0.001–7 weight % of EPC, and 30–99.9 weight % of water.

The topical dermal composition of the invention is preferably such that the alkyl side chain of the tocopheryl moiety of EPC has been included in a β-cyclodextrin or hydroxyalkylated β-cyclodextrin molecule to thereby reduce the surface activity of EPC-K and accordingly suppress foam production when dissolved in water and improve its stability against light.

BRIEF DESCRIPTION OF THE DRAWINGS

FIG. 1 is a schematic view illustrating the mechanism of reductions in surface activity and foam production of EPC-K;

FIG. 3 is a graph showing the relationship of the concentration of HP-β-CD with the time till disappearance of foam after shaking at a constant molar concentration of EPC-K;

FIG. 6 shows $^1$H-NMR spectra indicating the change in signals with variation of the EPC-K-to-HP-β-CD molar ratio;

DETAILED DESCRIPTION OF THE PREFERRED EMBODIMENTS

Figure 2A:
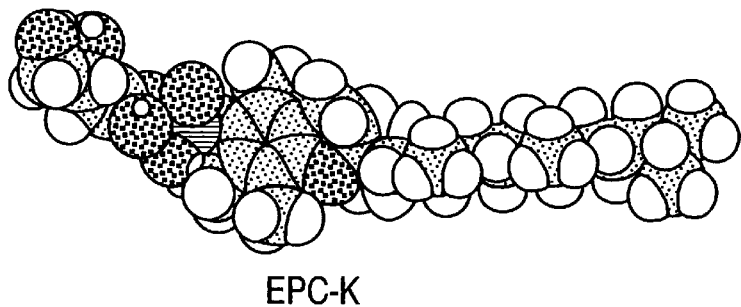
FIG. 2 shows CPK models illustrating the states of inclusion of EPC-K in HP-β-CD.
Figure 2B:
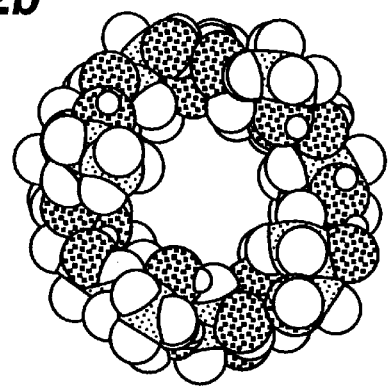
Figure 2C:
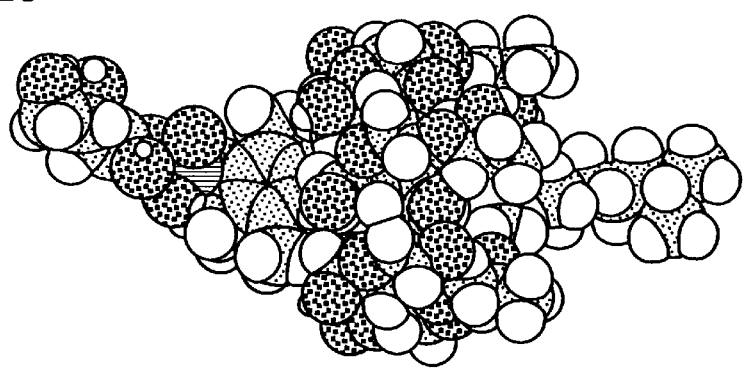
Figure 2D:
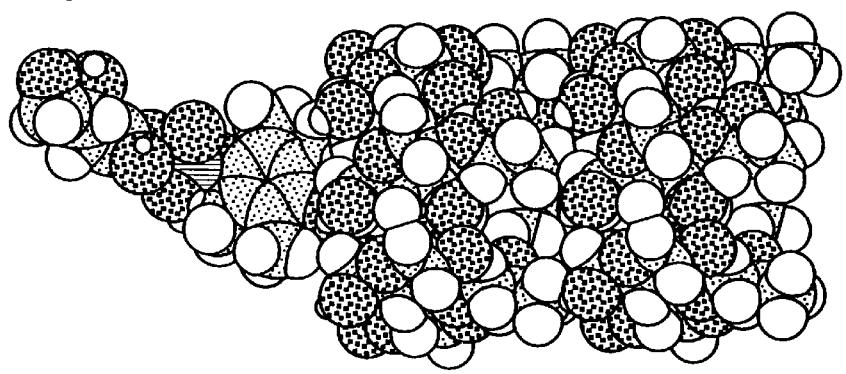

The present invention is now described in detail.

Cyclodextrin (hereinafter referred to briefly as CD) for use in the present invention is an oligosaccharide composed of glucose residues linked by α-1,4 linkages into a cyclic structure, and generally there are known α-CD consisting of 6 glucose residues, β-CD consisting of 7 glucose residues, and γ-CD consisting of 8 glucose residues. Each of those cyclodextrin species is capable of including a guest molecule suited to the size of its cavity. Since the guest molecule for use in the present invention is the alkyl side chain of the tocopheryl moiety of EPC, β-CD among them is suitable. Of course, a starch hydrolysate containing all of α-, β- and γ-CDs can be employed.

The hydroxyalkylated cyclodextrin (hereinafter referred to briefly as HACD) is a compound available on substitution of one or more hydroxyalkyl groups into the OH groups of a CD which is well known as a cyclic oligosaccharide. Thus, hydroxyalkyl groups are introduced into the OH— groups of CD to enhance the hydrophobicity of the cavity.

The hydroxyalkyl group that is generally used for substituting the OH groups of a CD includes hydroxyethyl and hydroxypropyl. By conducting this substitution reaction for OH groups, the objective HACD can be obtained. HACD includes hydroxyethylcyclodextrin, hydroxypropylcyclodextrin, hydroxybutylcyclodextrin, and dihydroxypropylcyclodextrin, among others.

The preferred degree of substitution of OH by hydroxyalkyl for the purposes of the invention is 1–14 per CD.

In consideration of the cost and ease of production, handlability, and water solubility, the preferred species of HACD are 2-hydroxyethyl-β-CD, 2-hydroxypropyl-β-CD, 3-hydroxypropyl-β-CD, and 2,3-dihydroxypropyl-β-CD, although those are not exclusive choices.

Several processes are known for the production of HACD. The following is a typical known process.

In 150 ml of 20% aqueous solution of NaOH is dissolved 100 g of β-CD (tradename: Celdex N, manufactured by Nihon Shokuhin Kako) and while the solution is held at 30° C., 50 ml of propylene oxide is added gradually dropwise. The reaction is carried out with stirring for 20 hours. This reaction mixture is neutralized with hydrochloric acid to pH 6.0, placed in a dialyzing tube, and desalted using running water for 24 hours. The desalted product is dried with a freeze dryer to provide about 90 g of hydroxypropylated β-CD. The degree of substitution of this hydroxypropylated β-CD is 5.1 per CD.

The guest EPC of the clathrate of the invention is dl-β-tocopherol (vitamin E) L-ascorbic acid (vitamin C) diester of phosphoric acid.

Ascorbic acid is of use as an anti-scurvy drug based on its collagen synthesis-stimulating activity, thus preventing deposition of melanoid pigments, the cause of freckles, and, as reported more recently, has anticancer activity. On the other hand, dl-α-tocopherol (vitamin E) has the property to activate the gonad and pituitary-adrenal system, stabilizes the plasma membrane of peripheral vascular endothelial cells, and reduces platelet aggregation and adhesion to improve peripheral circulation. Furthermore, dl-α-tocopherol has potent antioxidant activity to prevent damage of tissues by peroxylipids.

The technology for coupling those two biologically important substances, namely the water-soluble vitamin C (ascorbic acid) and the fat-soluble vitamin E (tocopherol), was developed and, as a consequence, the compound EPC consisting of one molecule each of those vitamins coupled in the form of phosphoric acid diester was synthesized.

EPC can be clathrated in the form of a salt and, as examples of such salt, the potassium (K) salt, sodium (Na) salt, and magnesium (Mg) salt can be mentioned. Preferred is the potassium salt (i.e. EPC-K).

Heretofore, fat-soluble vitamin E derivatives such as vitamin E acetate have been used as antioxidants but in order to use them a surfactant is required.

However, ionic surfactants such as alkyl sulfates and higher fatty acid salts are liable to irritate the skin when used in high concentrations. On the other hand, nonionic surfactants such as polyoxyethylene series surfactants inactivate antiseptics, such as hydroxybenzoic esters which are commonly formulated, and have the compatibility problem.

In contrast, EPC which is used in the present invention has high antioxidant activity and does not require a surfactant for dissolution in aqueous medium.

The above-mentioned clathrate consisting of EPC and a cyclodextrin or hydroxyalkylated cyclodextrin in a molar ratio of 1:1 or 1:2 (FIGS. 1 and 2) can be produced by mixing EPC with the cyclodextrin in water with stirring.

Thus, as the alkyl side chain of the oleophilic tocopheryl moiety of EPC-K is included in a β-cyclodextrin or hydroxyalkylated β-cyclodextrin molecule to thereby reduce said surface activity, foam production is suppressed and the light stability of the product is also improved. As mentioned above, this clathrate is a 1:1 or 1:2 clathrate consisting of EPC-K and either β-cyclodextrin or a hydroxyalkylated β-cyclodextrin.

By using this clathrate in a topical dermal composition, there can be obtained a pharmaceutical or cosmetic product with high stability and safety, reduced foam production, satisfactory light resistance, and good moisture-retaining and antioxidant properties. An emulsion containing this clathrate is preferably an oil-in-water emulsion and this is particularly true with cosmetic products.

An aqueous solution (e.g. a lotion) of this clathrate prepared without addition of a surfactant is also of value.

The EPC clathrate of the invention should be used in a sufficient amount to let its efficacy fully develop. The preferred proportion of the clathrate in a cosmetic composition is 0.001 to 10 weight % based on the total weight of the composition.

Except that the EPC clathrate of the invention is added, such a cosmetic composition can be manufactured in accordance with the established cosmetic production procedure.

In the present invention, within the range not interferring with the effect of the invention, excipients and other ingredients can be added according to the desired application form or type of product.

Thus, the cosmetic composition of the invention may contain a variety of additives including powdery substances such as titanium dioxide, mica powder, talc, kaolin, titanium dioxide-covered mica, etc.; natural oils of the vegetable or animal origin, such as primrose oil, avocado oil, mink oil, macademia nut oil, corn oil, rapeseed oil, castor oil, sunflower oil, cacao oil, coconut oil, rice bran oil, tsubaki oil, olive oil, lanolin, squalene, etc.; hydrocarbons such as liquid paraffin, squalane, white petrolatum, etc.; waxes such as paraffin wax, lanolin, jojoba oil, sperm wax, bees wax, candelilla wax, carnauba wax, etc.; higher alcohols such as cetanol, stearyl alcohol, isostearyl alcohol, 2-octyldodecanol, lanolin alcohol, etc.; higher fatty acids such as lauric acid, myristic acid, palmitic acid, stearic acid, behenic acid, isostearic acid, oleic acid, linolenic acid, linoleic acid, hydroxystearic acid, etc.; fatty acid esters such as isopropyl myristate, 2-octyldodecyl myristate, isopropyl palmitate, isopropyl stearate, glyceryl 2-ethylhexanoate, glyceryl tri(2-ethylhexanoate), cetyl 2-ethylhexanoate, diisostearyl malate, tetra(2-ethylhexane)pentaerythritol, etc.;

polar oils such as diethylene glycol monopropyl ether, polyoxyethylene polyoxypropylene pentaerythritol ether, polyoxypropylene butyl ether, ethyl linolate, etc.; silicone oils such as methylpolysiloxane, methylphenylpolysiloxane, etc.; thickners such as methylcellulose, gum arabic, polyvinyl alcohol, montmorillonite, rhaponite, carboxyvinyl polymer, alkyl-modified carboxyvinyl polymer, etc.; organic solvents such as ethanol, 1,3-butylene glycol, etc.; antioxidants and auxiliary antioxidants such as butylhydroxytoluene, tocopherol, butylhydroxyanisole, gallic acid esters, phytic acid, malic acid, etc.; antibacterial antiseptics such as benzoic acid, salicylic acid, sorbic acid, alkyl p-hydroxybenzoates (ethylparaben, butylparaben, etc.), hexachlorophene, etc.; nonionic surfactants such as sorbitan monolaurate, sorbitan sesquioleate, sorbitan trioleate, polyoxyethylated sorbitan monolaurate, polyethylene glycol monooleate, polyoxyethylene alkyl ethers, polyglycol diesters, lauroyldiethanolamide, fatty acid isopropanolamides, maltitol hydroxy-fatty acid ethers, alkylated polysaccharides, alkylglycosides, sugar esters, panthonyl ethyl ether, etc.; cationic surfactants such as stearyltrimethylammonium chloride, benzalkonium chloride, laurylamine oxide, etc.; anionic surfactants such as sodium palmitate, sodium laurate, potassium lauryl sulfate, alkyl sulfate triethanolamine ether, Turkey red oil, linear dodecylbenzenesulfonates, polyoxyethylated hydrogenated castor oil maleate, acylmethyl taurides, etc.; chelating agents such as EDTA sodium etc.; refresheners such as menthol, mint oil, peppermint oil, camphor, thymol inositol, spilanthol, methyl salicylate, etc.; colors; perfumes, and purified water. One or more of those ingredients can be selectively employed.

The preferred composition comprising the clathrate of the invention is as follows.

|  | Formulation amount (weight %) | Preferred range (weight %) |
| --- | --- | --- |
| Cyclodextrin | 0.005–20 | 1–5 |
| EPC-K | 0.001–7 | 0.005–0.2 |
| Deionized water | to 100 | to 100 |

The cosmetic composition of the present invention can be provided in a variety of application forms such as toilet water, vanishing cream, milk lotion, cold cream, cleansing cream, foundation cream, hand cream, cosmetic cocktail, and ointment, among others.

EXAMPLES

The following examples are merely intended to illustrate the present invention in further detail and should by no means be construed as defining the scope of the invention.

First, the inventors of the present invention studied the physicochemical properties of the EPC-K/hydroxyalkylated β-cyclodextrin clathrate of the invention. Thus, according to the following experimental protocol, the relationship of the concentration of 2-hydroxypropyl-β-CD (hereinafter referred to as HP-β-CD) with foam production was investigated using a fixed molar concentration of EPC-K. Experimental Protocol: Shaking test (evaluation of foam production) Instrument: Iuchi Shaker MW-1 Shaking conditions: 300 cycles/min.×20 min. The time till disappearance of foam (bubbles) was measured.

The results are presented in Table 1 and diagrammatically in FIG. 3. The formulation amounts in Table 1 are in M (=mol/L).

TABLE 1

|  | Comparative Example 1 | Example 1 | Example 2 | Example 3 |
| --- | --- | --- | --- | --- |
| EPC-K | 0.0002 | 0.0002 | 0.0002 | 0.0002 |
| HP-β-CD (2-hydroxypropyl-β-CD) | 0 | 0.0001 | 0.01 | 0.02 |
| Time till disappearance of foam | ≧3 days | 72 hr. | 2 hr. | 8 min. |

|  | Example 4 | Example 5 | Example 6 | Example 7 |
| --- | --- | --- | --- | --- |
| EPC-K | 0.0002 | 0.0002 | 0.0002 | 0.0002 |
| HP-β-CD (2-hydroxypropyl-β-CD) | 0.03 | 0.05 | 0.07 | 0.1 |
| Time till disappearance of foam | 3 min. | 1 min. | 30 sec. | 30 sec. |

It will be apparent from Table 1 and FIG. 3 that whereas the time till disappearance of foam after shaking was more than 3 days in the case of HP-β-CD-free formulation (Comparative Example 1), the time was curtailed as the concentration of HP-β-CD was increased and that, in Examples 5–7, the foam produced on shaking disappeared almost instantly. It is, thus, clear that HP-β-CD has the property to reduce the foam production associated with EPC-K.

Then, using the following experimental protocol, the relationship of the concentration of EPC-K with surface tension was investigated using a fixed molar concentration (3.6 mM) of HP-β-CD or in the absence (0.0 mM) of HP-β-CD.

Measurement of surface tension (25° C.)
Instrument: Shimadzu Surface Tension Meter ST-1

Figure 4:
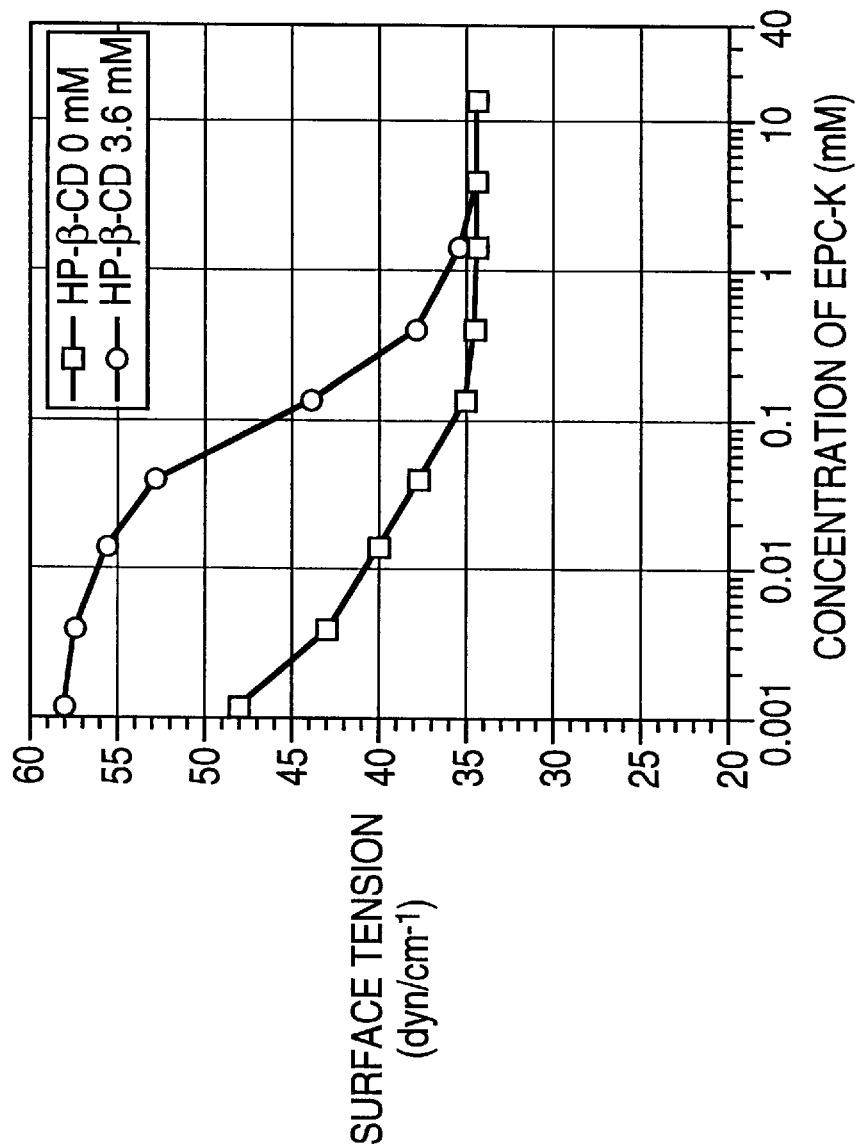
FIG. 4 is a diagram showing the relationship of the concentration of EPC-K with the surface tension of its solution in the presence or absence of HP-β-CD.

The results are presented diagrammatically in FIG. 4. It will be apparent from FIG. 4 that HP-β-CD remarkably interferes with the surface activity of EPC-K. This result indicates that inclusion of the alkyl side chain of tocopheryl (vitamin E) moiety of EPC-K in the cyclodextrin molecule as illustrated in the model of FIG. 1 reduces the surface activity of EPC-K and thereby inhibits foam production.

Then, the state of clathration was examined by $^1$H-NMR spectrometry.

Figure 5A:
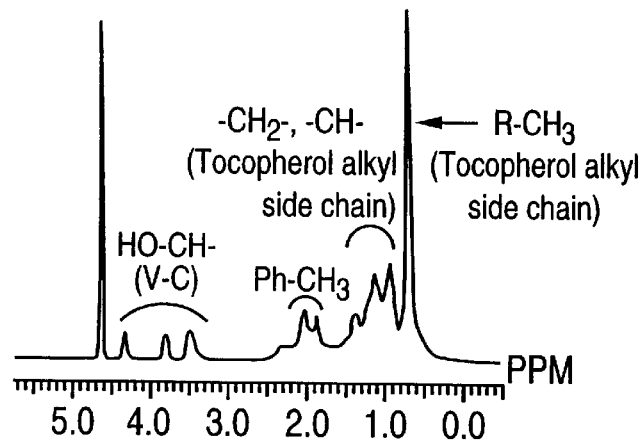
FIG. 5 shows $^1$H-NMR spectra of EPC-K alone, EPC-K:HP-β-CD=1:1 (molar ratio), and HP-β-CD alone.
Figure 5B:
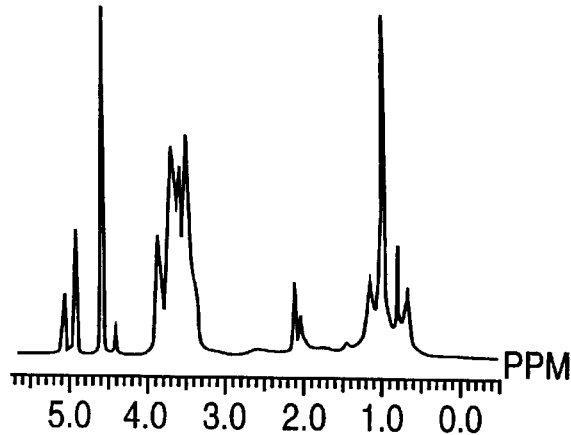
Figure 5C:
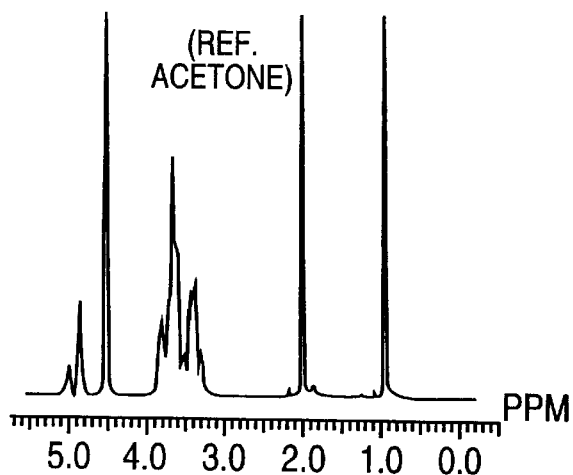
Figure 7A:
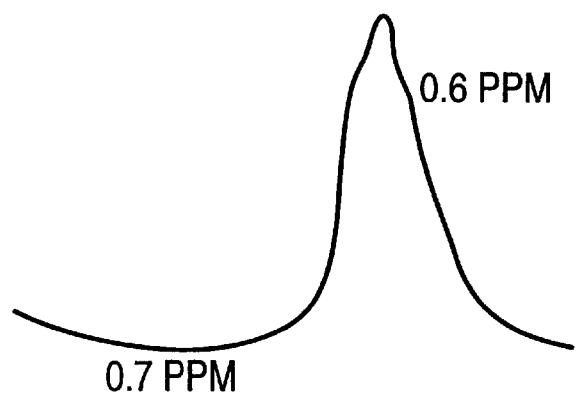
FIG. 7 shows the $^1$H-NMR spectra on exaggerated scale, indicating the change in the peak assignable to the alkyl side chain Me protons of the tocopheryl moiety of EPC-K at 0.6–0.7 ppm with variation of the EPC-K-to-HP-β-CD molar ratio.
Figure 7B:
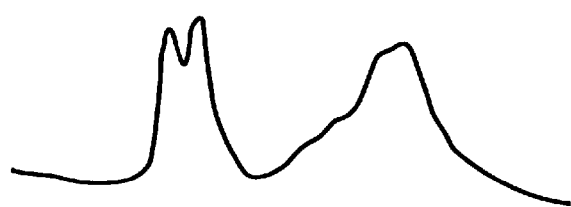
Figure 7C:
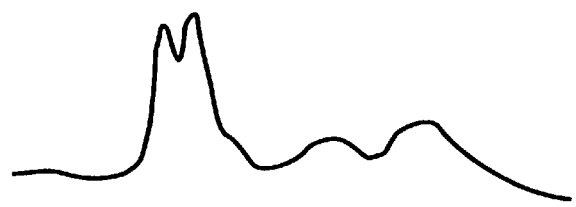
Figure 7D:
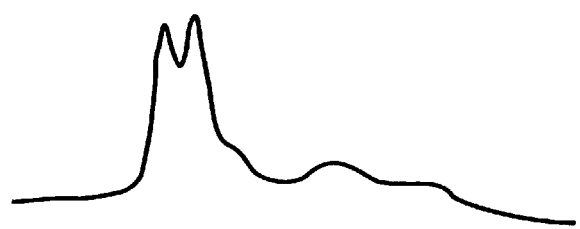
Figure 7E:
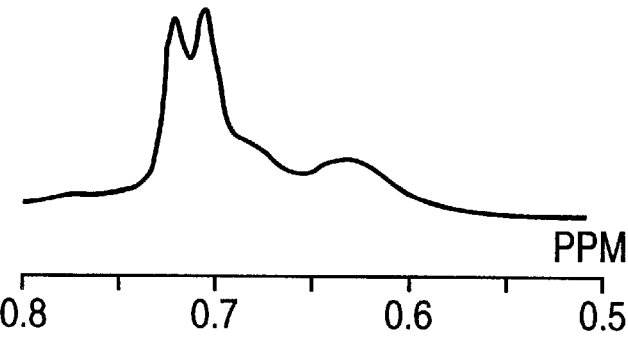
Figure 8A:
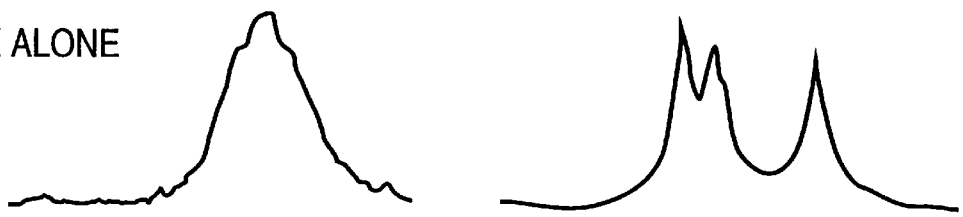
FIG. 8 shows the $^1$H-NMR spectra on exaggerated scale, indicating the changes in the peak assignable to the Ph-Me protons of the tocopheryl moiety at 1.7–2.1 ppm and the peak assignable to the —CH— protons of the ascorbyl moiety at 4.2–4.4 ppm with variation of the EPC-K-to-HP-β-CD molar ratio.
Figure 8B:
Figure 8C:
Figure 8D:
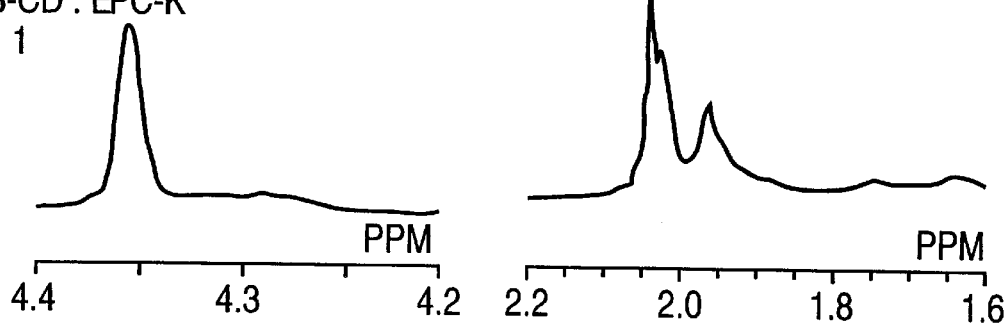

The measuring conditions were as follows.
$^1$H-NMR spectrometer:
Japan Electronics JNM-EX400, Slv. $D_2O$
Samples: 1) EPC-K 10 mM/$D_2O$
2) EPC-K+HP-β-CD 10 mM/$D_2O$
3) HP-β-CD 10 mM/$D_2O$ The NMR spectra are shown in FIG. 5. Comparison of the spectrum of EPC-K alone with the spectrum of EPC-K/hP-β-CD=1:1 shows changes in the peaks assignable to the alkyl side chain Me protons of the tocopheryl moiety of EPC-K at 0.6–0.7 ppm, the Phe-Me protons of the tocopheryl moiety at 1.7–2.1 ppm, and the —CH— protons of the ascorbyl moiety at 4.2–4.4 ppm.

Then, those NMR signals were scrutinized by varying the molar ratio. FIG. 6 shows the spectra recorded with varying molar ratios and FIG. 7 shows the peak of the alkyl side chain Me protons of the tocopheryl moiety of EPC-K at 0.6–0.7 ppm on exaggerated scale. FIG. 8 shows the peaks assignable to the Ph-M protons of the tocopheryl (vitamin E) moiety at 1.7–2.1 ppm and the —CH— protons of the ascorbyl (vitamin C) moiety at 4.2–4.4 ppm on exaggerated scale.

It will be apparent from FIGS. 6–8 that as the proportion of HP-β-CD was increased, the peak of the alkyl side chain Me protons of the tocopheryl moiety at 0.6 ppm was gradually eliminated, with appearance of a peak at 0.7 ppm and a broad signal at 0.63–0.7 ppm. Moreover, the signal of the —CH— protons of the ascorbyl (vitamin C) moiety at 4.25 ppm was gradually shifted to 4.35 ppm.

Figure 9A:
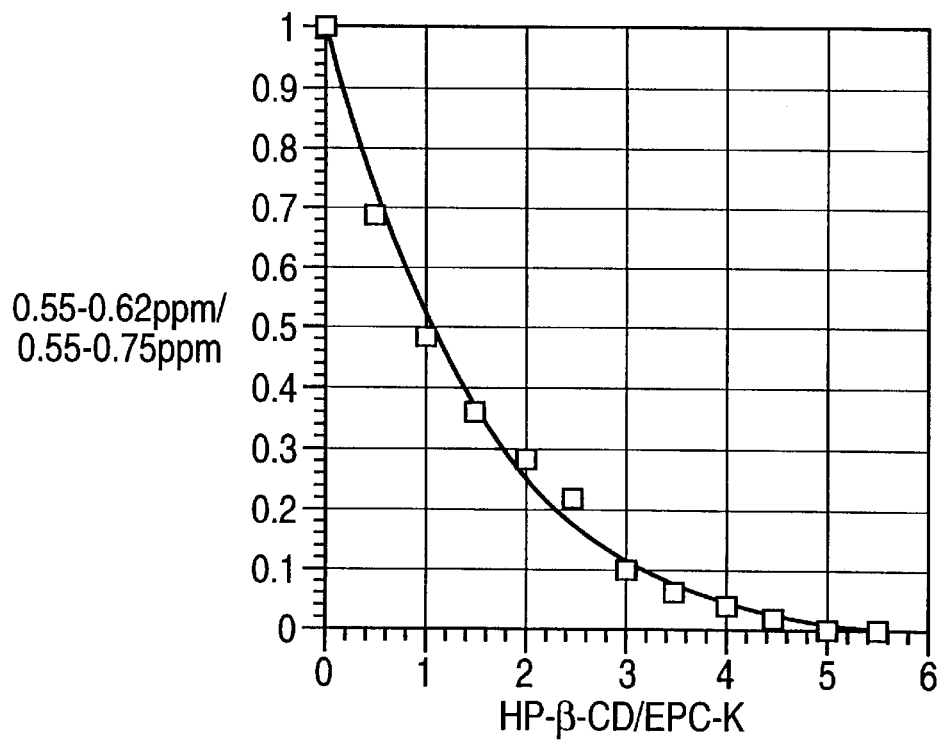
FIG. 9 is a diagram showing the relationship of the rate of shift of the peak assignable to the alkyl side chain Me protons of the tocopheryl (vitamin E) moiety of EPC-K at 0.6–0.7 ppm and the rate of shift of the peak assignable to the —CH— protons of the ascorbyl (vitamin C) moiety at 4.2–4.4 ppm, both as plotted against HP-β-CD/EPC-K molar ratio.
Figure 9B:
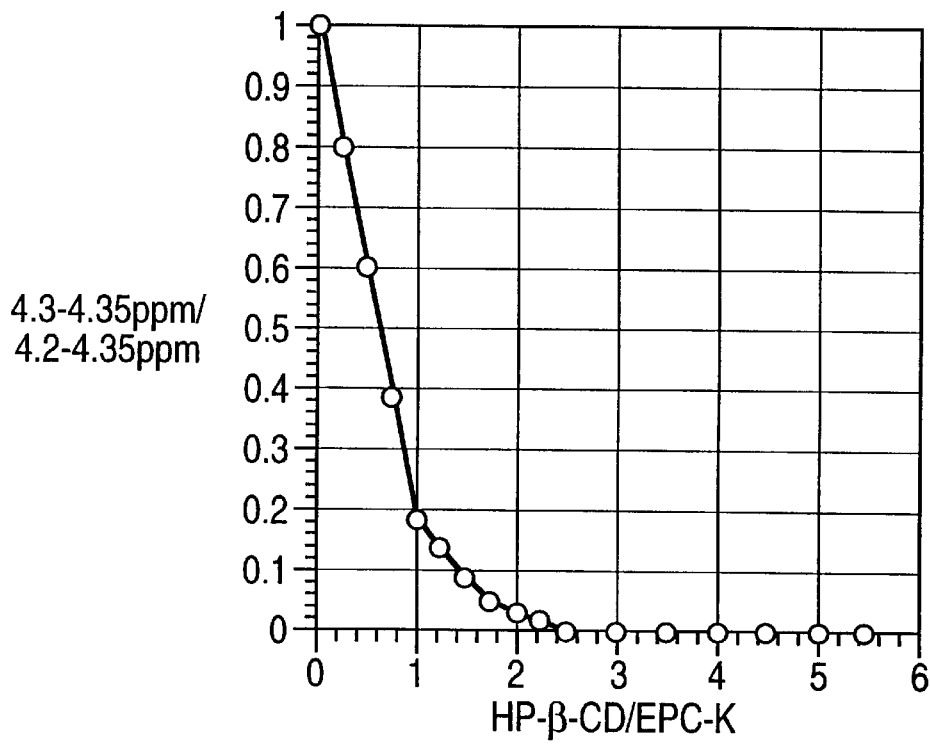

The relationship of the rates of shift of those signals with the HP-β-CD/EPC-K molar ratio is shown in FIG. 9.

It will be apparent from FIG. 9 that the rate of disappearance of the peak assignable to the alkyl chain Me protons of the tocopheryl (vitamin E) moiety at 0.6 ppm is different from the rate of disappearance of the peak assignable to the —CH— protons of the ascorbyl (vitamin C) moiety at 4.25 ppm. This discrepancy does not occur when the molar ratio of HP-β-CD to the guest molecule is 1:1. It is, therefore, thought that a complex was formed in the molar ratio of not less than 2:1. As will be understood from the CPK model presented in FIG. 2, it appears structurally difficult to form a clathrate of a 3:1 or greater ratio. It is, therefore, considered that HP-β-CD and EPC-K formed a complex with a molar ratio of 2:1.

The effect on foam production and light stability (discoloration) of HP-β-CD were investigated in a simple cosmetic formulation. The results are presented in Table 2. The formulation amounts are in weight %.

Test protocol

Foam production: The time till disappearance of foam after shaking

Method: Shaking test

Instrument: IUCHI Shaker MW-1

Test conditions: 300 cycles/min., 20 min. The time till disappearance of foam after shaking was measured.

Light stability: Xe irradiation (accelerated test); the color difference is measured.

Method: A sample exposed to Xe light for 30 hours at 50° C. was compared with an unexposed control sample.

Xe irradiation: Xenon Long Life Fade Meter (50° C., 30-hour exposure), Suga Test Instruments Co. Ltd.

Color difference: S&M Color Computer Model SM-4, Suga Test Instruments Co. Ltd.

TABLE 2

|  | Comparative Example 2 | Example 8 | Example 9 | Example 10 |
|---|---|---|---|---|
| EPC-K | 0.01 | 0.01 | 0.01 | 0.01 |
| HP-β-CD | — | 2 | 5 | — |
| β-CD | — | — | — | 1.5 |
| Denaturated synthetic alcohol | 5 | 5 | 5 | 5 |
| Deionized water | 94.84 | 92.84 | 89.84 | 93.34 |
| Methyl p-hydroxy benzoate | 0.15 | 0.15 | 0.15 | 0.15 |
| Time till disappearance of foam | ≧3 Days | 2 Hr. | 5 Min. | 3 Hr. |
| Xe irradiation-color difference (ΔE) | 7.28 | 3.81 | 0.82 | 4.32 |

It will be apparent from Table 2 that whereas the time till disappearance of foam after shaking was not less than 3 days in Comparative Example 2 corresponding to omission of HP-β-CD or β-CD, the time was considerably decreased in Examples 8–10 in which HP-β-CD or β-CD was added. Improvements were also obtained in light stability as tested by the Xe irradiation method.

More specific examples of the invention are shown below. All the formulation amounts are in weight %. Incidentally, in each of the following examples, disappearance of foam after shaking was rapid and the light stability of each formulation was satisfactory.

Example 11

Toilet water

| A. Aqueous part | |
|---|---|
| BPC-K | 0.01% |
| 2-Hydroxypropyl-β-CD | 4.0 |
| Glycerin (Dynamit) | 4.0 |
| Propylene glycol | 3.0 |
| Citric acid | 0.02 |
| Sodium citrate | 0.05 |
| Sodium tetrametaphosphate | 0.02 |
| Purified water | Balance |
| B. Alcoholic part | |
| Denatured synthetic alcohol | 5.0 |
| Methyl p-hydroxybenzoate | 1.5 |
| Perfume | q.s. |

(Production process)

EPC-K, HP-β-CD, a humectant, etc. are added to purified water and the mixture is stirred with a propeller mixer for 10 minutes to dissolve thoroughly. This solution is used as the main part. On the other hand, a preservative and a perfume are added to denatured synthetic alcohol to prepare a homogeneous solution. This solution is added to the main part and the mixture is stirred with a propeller mixer for 10 minutes to provide a toilet water.

Example 12

Toilet water

| A. Aqueous part | |
|---|---|
| EPC-K | 0.01% |
| β-CD | 1.5 |
| Glycerin (Dynamit) | 7.0 |
| 1,3-Butylene glycol | 4.0 |
| Citric acid | 0.02 |
| Sodium citrate | 0.05 |
| Sodium hydroxymethoxybenzophenone-sulfonate | 0.05 |
| Purified water | Balance |
| B. Alcoholic part | |
| Denatured synthetic alcohol | 7.0 |
| Methyl p-hydroxybenzoate | 1.5 |
| Perfume | q.s |

(Production process)

A toilet water is produced by the same procedure as Example 11.

Example 13

Toilet water

| A. Aqueous part | |
|---|---|
| EPC-K | 0.02% |
| Hydroxyethyl-β-CD) | 4.0 |
| Glycerin (Dynamit) | 5.0 |
| 1,3-Butylene glycol | 5.0 |
| Citric acid | 0.02 |
| Sodium citrate | 0.05 |
| Sodium hydroxymethoxybenzophenone-sulfonate | 0.05 |
| Sodium hexametaphosphate | 0.02 |
| Purified water | Balance |

-continued

| B. Alcoholic part | |
| --- | --- |
| Denatured synthetic alcohol | 7.0 |
| Methyl p-hydroxybenzoate | 1.5 |
| Perfume | q.s |

(Production process)

A toilet water is produced by the same procedure as Example 11.

Example 14
Cosmetic Lotion

| A. Aqueous part | |
| --- | --- |
| EPC-K | 0.01% |
| 3-Hydroxypropyl-β-CD | 3.0 |
| Glycerin (Dynamit) | 6.0 |
| Propylene glycol | 5.0 |
| Ethanol | 3.0 |
| Methyl p-hydroxybenzoate | 0.2 |
| Polyoxyethylene(60)-hydrogenated castor oil | 0.2 |
| Carboxyvinyl polymer | 0.15 |
| Purified water | Balance |
| B. Oily part | |
| Liquid paraffin | 1.5 |
| Squalene | 2.0 |

(Production process)

EPC-K, HP-β-CD, and a humectant are added to purified water and the mixture is stirred with a propeller mixer to dissolve thoroughly. This solution is used as the main part. The oily part is added to the main part and the mixture is stirred with a homomixer for 10 minutes to provide a cosmetic lotion.

As described in detail hereinbefore, the EPC/CD clathrate of the invention is a complex compound in which the alkyl side chain of the oleophilic tocopheryl moiety of EPC, which is mainly responsible for foam production in aqueous solution and poor light stability, has been included in a cyclodextrin or hydroxyalkylated cyclodextrin molecule to reduce foam production and improve light stability.

Furthermore, the topical dermal composition of the present invention makes it possible to use EPC having humectant and antioxidant properties in stabilized form in an aqueous system such as a toilet water.

In addition, EPC, a vitamin E derivative, can now be safely formulated without the aid of a surfactant which has heretofore been indispensable and, moreover, there is no risk of skin irritation.

What is claimed is:

1. A clathrate comprising a cyclodextrin or hydroxyalkylated cyclodextrin and, as included therein, dl-α-tocopheryl L-ascorbyl phosphate in a molar ration of 1:1–2:1.

2. The clathrate claimed in claim 1 wherein said cyclodextrin or hydroxyalkylated cyclodextrin is β-cyclodextrin or a hydroxyalkylated β-cyclodextrin.

3. A topical dermal composition containing the clathrate claimed in claim 1.

4. The topical dermal composition claimed in claim 3 which is an oil-in-water emulsion.

5. The topical dermal composition claimed in claim 3 which is an aqueous solution prepared without addition of a surfactant.

6. The topical dermal composition as claimed in claim 3 containing the clathrate in a proportion of 0.001 to 10 weight percent based on the total weight of the composition.

7. A cosmetic composition comprising a cyclodextrin and/or a hydroxyalkylated cyclodextrin and dl-α-tocopheryl L-ascorbyl phosphate in a molar ration of 1:1–2:1.

8. The topical dermal composition as claimed in claim 5 comprising 0.005 to 20 weight % of β-cyclodextrin or hydroxyalkylated β-cyclodextrin, 0.001–7 weight % of dl-α-tocopheryl L-ascorbyl phosphate, and 30–99.9 weight % of water.

9. A topical dermal composition comprising a dl-α-tocopheryl L-ascorbyl phosphate-β-cyclodextrin or hydroxyalkylated β-cyclodextrin clathrate wherein the alkyl side chain of the tocopheryl moiety of said dl-α-tocopheryl L-ascorbyl phosphate has been included in said β-cyclodextrin or hydroxyalkylated β-cyclodextrin to reduce the surface activity of dl-α-tocopheryl L-ascorbyl phosphate the molar ratio of—cyclodextrin or hydroxylated β-cyclodextrin to dl-α-tocopherol L ascorbyl phosphate being 1:1–2:1.

* * * * *